United States Patent
Sakaguchi

(10) Patent No.: US 9,883,976 B2
(45) Date of Patent: Feb. 6, 2018

(54) DISPOSABLE DIAPER WITH SHEET-SHAPED ELASTIC MEMBER

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 703 days.

(21) Appl. No.: 14/368,731

(22) PCT Filed: Dec. 28, 2012

(86) PCT No.: PCT/JP2012/084112
§ 371 (c)(1),
(2) Date: Jun. 25, 2014

(87) PCT Pub. No.: WO2013/100135
PCT Pub. Date: Jul. 4, 2013

(65) Prior Publication Data
US 2015/0005730 A1    Jan. 1, 2015

(30) Foreign Application Priority Data
Dec. 28, 2011    (JP) ................... 2011-289647

(51) Int. Cl.
*A61F 13/15* (2006.01)
*A61F 13/20* (2006.01)
(Continued)

(52) U.S. Cl.
CPC .. *A61F 13/49011* (2013.01); *A61F 13/49413* (2013.01); *A61F 13/53* (2013.01); *A61F 2013/4948* (2013.01)

(58) Field of Classification Search
CPC ... A61F 13/53; A61F 13/535; A61F 13/49007
See application file for complete search history.

(56) References Cited

U.S. PATENT DOCUMENTS 4,642,110 A    2/1987 Dudek
4,685,916 A    8/1987 Enloe
(Continued)

FOREIGN PATENT DOCUMENTS

CN    101090681 A    12/2007
CN    1207663 A    11/2012
(Continued)

OTHER PUBLICATIONS

Office Action in GCC Application No. GC2012-23241, dated May 16, 2016.
(Continued)

*Primary Examiner* — Michele M Kidwell
(74) *Attorney, Agent, or Firm* — Hauptman Ham, LLP

(57) ABSTRACT

A disposable diaper 10 includes a sheet-like elastic element 100 provided in a rear waistline portion 30. The sheet-like elastic element 100 has a stretching portion 105 that can be stretched in a product width direction W. An absorber 40 includes a low rigidity portion 110, where the basis weight is lower than those in the other parts of the absorber 40 or an absorber core 40a does not exist, and a non-stretching portion 45 that is unstretchable in the product width direction W. The non-stretching portion 45 is provided at a crotch portion side from the stretching portion 105, and the stretching portion 105 overlaps at least a part of the low rigidity portion 110 in the plan view of the disposable diaper 10, and the width of the low rigidity portion 110 in the product width direction W widens towards the end at the side of the rear waistline portion 30 in a product longitudinal direction L.

10 Claims, 5 Drawing Sheets

(51) Int. Cl.
 *A61F 13/49* (2006.01)
 *A61F 13/53* (2006.01)
 *A61F 13/494* (2006.01)

(56) References Cited

U.S. PATENT DOCUMENTS

| | | | |
|---|---|---|---|
| 4,704,116 A * | 11/1987 | Enloe | A61F 13/49009 604/358 |
| 4,762,521 A | 8/1988 | Roessler et al. | |
| 5,358,500 A | 10/1994 | Lavon et al. | |
| 6,827,806 B2 | 12/2004 | Uitenbroek et al. | |
| 2003/0111166 A1 | 6/2003 | Uitenbroek et al. | |

FOREIGN PATENT DOCUMENTS

| | | |
|---|---|---|
| EP | 1 829 514 A1 | 9/2007 |
| JP | 63-11151 A | 1/1988 |
| JP | 2003-38553 A | 2/2003 |
| JP | 2007-268215 A | 10/2007 |
| JP | 2008-113684 A | 5/2008 |
| JP | 2008-525149 A | 7/2008 |
| JP | 2008-253289 A | 10/2008 |
| JP | 2011-072659 A | 4/2011 |
| TW | 530635 U | 5/2003 |
| WO | 2006/007008 A1 * | 1/2006 ............ A61F 13/15 |
| WO | 2011/077666 A1 | 6/2011 |

OTHER PUBLICATIONS

Office Action in CN Patent Application No. 201410644027.4, dated May 5, 2016.
Office Action in EA Patent Application No. 201400752, dated Jun. 23, 2016.
Office Action in AU Patent Application No. 2012361440 dated Jul. 1, 2016.
Office Action in EA Application No. 201400752 dated Feb. 3, 2016.
Office Action dated Aug. 4, 2015 corresponding to Japanese patent application No. 2013-097767.
International Search Report dated Feb. 26, 2013 in International Application No. PCT/JP2012/084112, filed Dec. 28, 2012.
Chinese Office Action dated Mar. 21, 2014 in corresponding Chinese Application No. 201280016701.3.
Office Communication in corresponding ROC Application No. 101150547 completed Feb. 18, 2014.
Extended European Search Report dated Aug. 19, 2015, corresponding to European patent application No. 12863022.5.
Office Action in CN Patent Application No. 201410644027.4 dated Jul. 7, 2017. 13pp.

* cited by examiner

US 9,883,976 B2

DISPOSABLE DIAPER WITH SHEET-SHAPED ELASTIC MEMBER

RELATED APPLICATIONS

The present application is a National Phase of International Application Number PCT/JP2012/084112, filed Dec. 28, 2012, and claims priority from Japanese Application No. JP 2011-289647 filed Dec. 28, 2011.

TECHNICAL FIELD

The present invention relates to a disposable diaper including an absorber spanning a crotch portion and extending in a front waistline portion and a rear waistline portion.

BACKGROUND ART

Conventionally, in order to achieve a wearing comfort while preventing the leakage of bodily waste, various efforts have been made for a disposable diaper. For example, various structures are proposed to improve the fitting of the disposable diaper to the hips of the wearer.

In the disposable diaper described in Patent Literature 1, in order to enable a raised portion formed in a rear waistline portion to easily enter the caved portion (anal cleft) of the hips, a structure in which elastic members provided in the rear waistline portion are given an almost V-shape towards the crotch side at the central portion in the product width direction has been adopted.

Furthermore, in a disposable diaper described in Patent Literature 2, in order to make an exterior sheet stretchable in the portions corresponding to the left side of the left hips, the sacrococcygeal portion, and the right side of the right hips in the rear waistline portion of the exterior sheet, a structure in which a plurality of elastic members are provided along the product width direction and at an interval in the product longitudinal direction has been adopted.

However, the aforementioned conventional disposable diaper had the below problems. That is, a problem of the disposable diaper described in Patent Literature 1 is that the raised portion enters the caved portion of the hips, and thus, friction is generated easily between the raised portion and the surface of the skin when the wearer moves his or her body, resulting in a feeling of discomfort being given to the wearer and a stronger stimulation being applied to the skin of the wearer. Another problem of the disposable diaper is that it stretches in the product longitudinal direction as well, and thus a shift in the position occurs easily in the product longitudinal direction, which is likely to result in leakage of bodily waste.

A problem of the disposable diaper described in Patent Literature 2 is that the absorbing portion of the disposable diaper is in close contact with the caved portion of the hips, and thus, a feeling of discomfort is given to the wearer and a stronger stimulation is applied to the skin of the wearer. In addition, in the disposable diaper, elastic members are provided across portions which correspond to the left side of the left hips, the sacrococcygeal portion, and the right side of the right hips, respectively, and thus, the wearer and the disposable diaper are in close contact each other in order to retain bodily waste such as stool. As a result, it becomes difficult to retain the bodily waste in the disposable diaper, thus causing a concern over induction of leakage from the side of the leg hole openings.

Furthermore, the conventional disposable diaper has been designed based on the posture when the wearer stands upright or the posture when the wearer lies on his or her back, and postures unique to infants have not been sufficiently considered. Therefore, the disposable diaper cannot run along the body in the sacral portion of the wearer, easily resulting in a gap between the body and the disposable diaper. Particularly, when an infant adopts a so-called C-shaped curved posture, that is, a posture where the back is curved, such as when the legs are raised or when the infant is held in arms, there tends to cause a problem that the diaper is shifted and a gap occurs around the lower back at the dorsal side.

CITATION LIST

Patent Literature

PTL 1: Japanese Patent Application Publication No. 2008-253289 (FIG. 1 and FIG. 2)
PTL 2: Japanese Patent Application Publication No. 2007-268215 (FIG. 4)

SUMMARY OF INVENTION

A first feature of the present invention is summarized as a disposal diaper (disposal diaper 10), comprising: a front waistline portion (front waistline portion 20), a rear waistline portion (rear waistline portion 30), a crotch portion (crotch portion 25) positioned between the front waistline portion and the rear waistline portion; and an absorber (absorber 40) spanning the crotch portion and extending in the front waistline portion and the rear waistline portion; and having a product longitudinal direction (product longitudinal direction L) from the front waistline portion towards the rear waistline portion, and a product width direction (product width direction W) perpendicular to the product longitudinal direction, the disposal diaper comprising a sheet-like elastic element (sheet-like elastic element 100) provided in the rear waistline portion is included, wherein the sheet-like elastic element includes a stretching portion configured to be stretchable in the product width direction, and the absorber comprises: a low rigidity portion (low rigidity portion 110) where a basis weight is lower than a basis weight in the other parts of the absorber or an absorber core does not exist, and a non-stretching portion (non-stretching portion 45) that is unstretchable in the product width direction, and the non-stretching portion is provided at side of the crotch portion from the stretching portion, the stretching portion overlaps at least a part of the low rigidity portion in a plan view of the disposable diaper, the low rigidity portion extends up to the end at the side of the rear waistline portion of the absorbent core, and the width of the low rigidity portion in the product width direction widens towards the end at side of the rear waistline portion in the product longitudinal direction.

DESCRIPTION OF EMBODIMENTS

Figure 1:
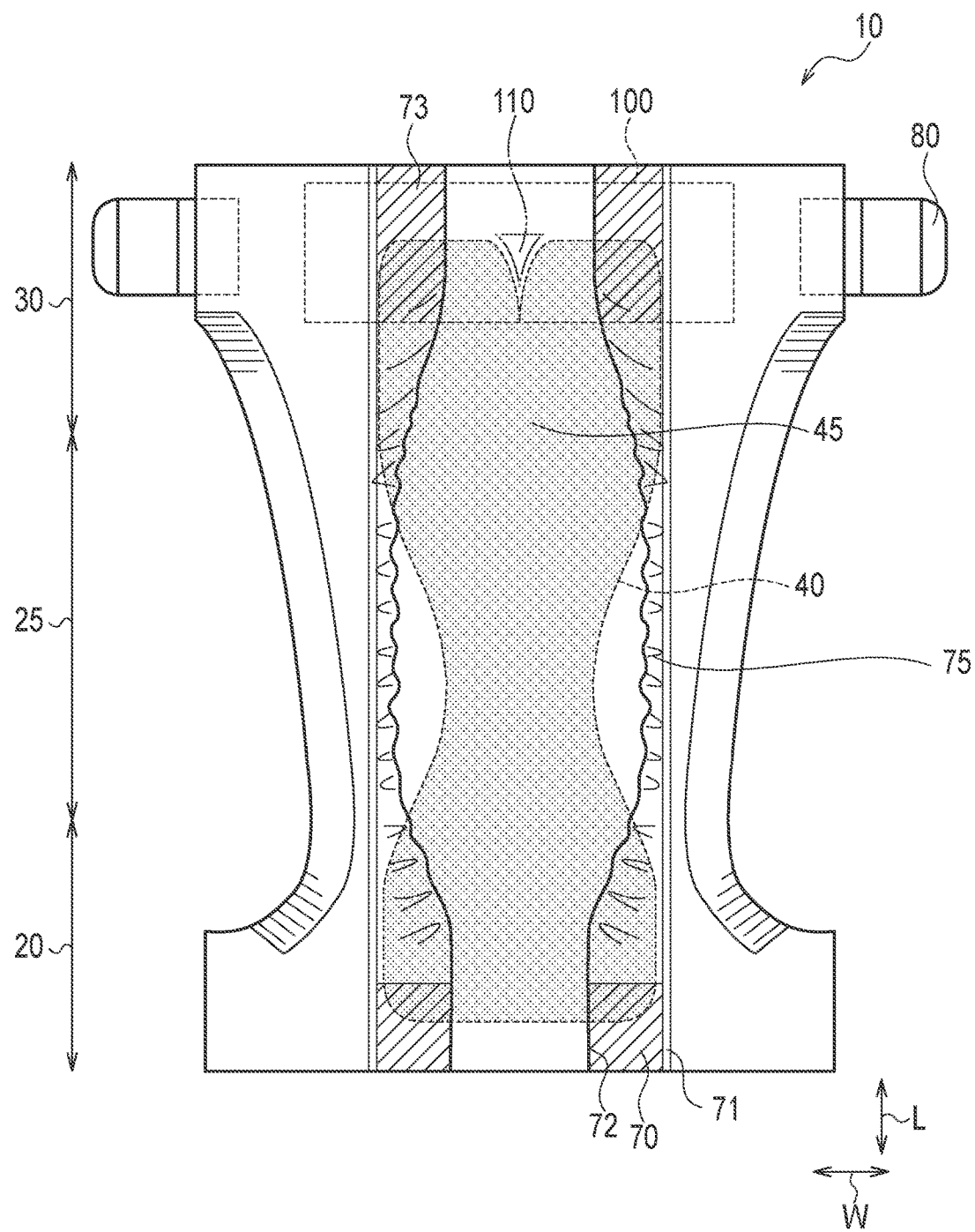
FIG. 1 is an exploded plan view of a disposable diaper 10 according to an embodiment.

Next, an embodiment of a disposable diaper according to the embodiment is explained with reference to drawings. In the following description of the drawings, the same or similar reference numerals are used to designate the same or similar parts. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Overall Schematic Configuration of Disposable Diaper

Figure 2:
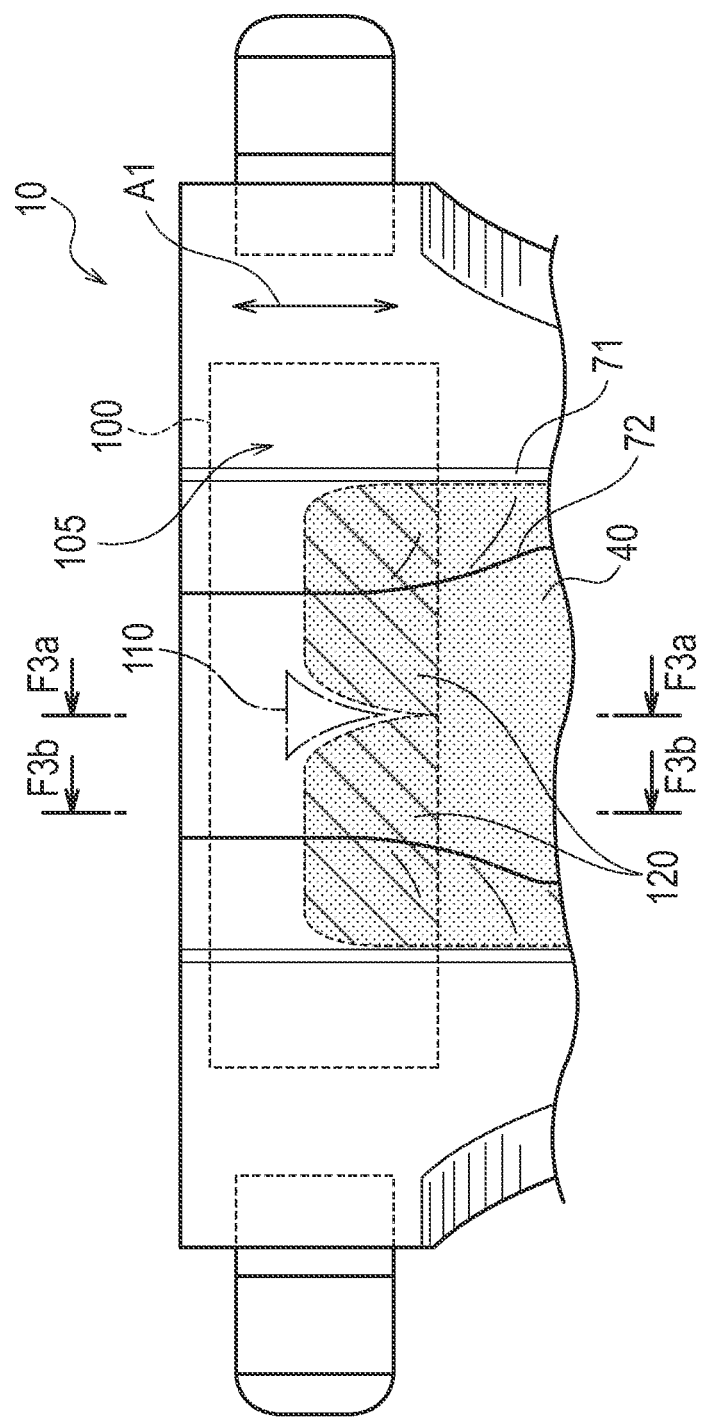
FIG. 2 is an enlarged plan view of a part of a rear waistline portion of the disposable diaper 10 according to an embodiment.
Figure 3A:
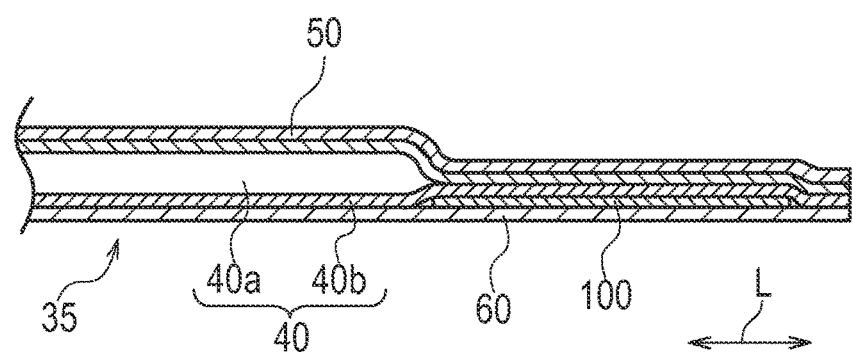
FIG. 3 is a cross-sectional view of the disposable diaper 10 along the F3a-F3a line, and a cross-sectional view of the disposable diaper 10 along the F3b-F3b line illustrated in FIG. 2.
Figure 3B:
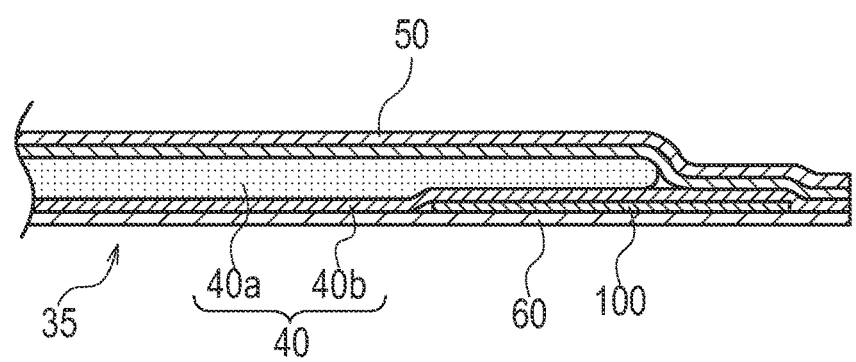

FIG. 1 is an exploded plan view of a disposable diaper 10 according to the present embodiment. FIG. 2 is an enlarged plan view of a part of a rear waistline portion of the disposable diaper 10. FIGS. 3(*a*) and (*b*) are a cross-sectional view of the disposable diaper 10 along the F3*a*-F3*a* line, and a cross-sectional view of the disposable diaper 10 along the F3*b*-F3*b* line, respectively, illustrated in FIG. 2.

As illustrated in FIG. 1 through FIG. 3, the disposable diaper 10 includes a front waistline portion 20 and a rear waistline portion 30. Furthermore, the disposable diaper 10 includes a crotch portion 25 positioned between the front waistline portion 20 and the rear waistline portion 30. The front waistline portion 20 is a portion that is in contact with the front waistline part of the wearer and the rear waistline portion 30 is the portion that is in contact with the rear waistline part of the wearer. The crotch portion 25 is the portion that is in contact with the crotch of the wearer. In the present embodiment, the direction from the front waistline portion 20 to the rear waistline portion 30 is called the product longitudinal direction L, and the direction perpendicular to the product longitudinal direction L is called the product width direction W.

The disposable diaper 10 is provided with an absorber 40 that includes an absorbent core 40*a* provided from the front waistline portion 20 across the rear waistline portion 30. The absorbent core 40*a* is the same as in the conventional disposable diaper, and can be configured appropriately by using popular components and materials, such as ground pulp and high absorbent polymer. The absorbent core 40*a* is wrapped by a sheet-like core wrap 40*b*. The core wrap 40*b* is a sheet of any optional material through which liquids pass. For example, a tissue sheet, or a spun bond nonwoven cloth and SMS (spun bond-meltblown-spun bond) nonwoven cloth may be used as the core wrap 40*b*.

On the top side (skin contact surface side) of the absorber 40 is provided a liquid-permeable topsheet 50. Furthermore, on the back side (non-skin contact surface side) of the absorber 40 is provided a liquid-impermeable backsheet 60.

A pair of left-right solid gathers 70 is provided at the top surface side of the absorber 40. The solid gathers 70 extend along the product longitudinal direction in both side edges in the product width direction W of the absorber 40. The solid gathers 70 extend along the product longitudinal direction L in both side edges in the product width direction W of the absorber 40, and include a fixed end 71 fixed on an absorbent chassis 35 including the absorber 40 and a free end 72 rising from the absorbent chassis 35. In the present embodiment, the solid gathers 70 configure a pair of longitudinal elastic elements.

The free end 72 is fixed on the topsheet 50 along with the fixed end 71, at the end in the product longitudinal direction L. The solid gathers 70 are fixed at a position overlapping the absorber 40, specifically, the absorbent core 40*a*, at an end 73 (the portion indicated by hatching in FIG. 1) at the side of the rear waistline portion 30.

Furthermore, the absorbent chassis 35 includes a pair of left-right leg gathers 75 is included at the outer side in the product width direction W of the solid gathers 70. The disposable diaper 10 may include waist gathers arranged along the product width direction W in the front waistline portion 20 and the rear waistline portion 30.

A pair of fastening tapes 80 is included in the rear waistline portion 30. The fastening tapes 80 are configured to extend at the outer side of the absorber 40 in the width direction from the rear waistline portion 30 to be affixed to the front waistline portion 20. The fastening tapes 80 may be provided in the front waistline portion 20.

Furthermore, the disposable diaper 10 includes a sheet-like elastic element 100 having a stretching portion 105 that can be stretched in the product width direction W. The sheet-like elastic element 100 is provided in the rear waistline portion 30.

The absorber 40 includes a low rigidity portion 110, where the basis weight is lower than the other parts of the absorber 40 or the absorbent core 40*a* does not exist. Additionally, the absorber 40 includes a stretch control portion 120, which is the portion where the stretch in the product width direction W is more controlled than that in the other portions (the portion indicated by hatching in FIG. 2).

Note that, the basis weight of the absorber is measured by the following procedure. Firstly, a measurement sample of rectangular shape is prepared, by cutting a measurement target portion, having a length of 1 cm in the product longitudinal direction and a length of 1 cm in the product width direction, from the absorber. Secondly, a weight (g) of the measurement sample is measured using an electronic balance, and the basis weight ($g/cm^2$) of the measurement sample is calculated, by dividing the measured weight by an area of the measurement sample (1 cm×1 cm=1 $cm^2$). Thirdly, above measurement is performed for five different measurement samples, the average value of the five measurement samples is calculated as the basis weight of the measurement target portion.

The sheet-like elastic element 100 overlaps at least a part of the low rigidity portion 110 in the plan view of the disposable diaper 10. Furthermore, the low rigidity portion 110 extends up to the end at the side of the rear waistline portion 30 of the absorbent core 40*a*.

The width of the low rigidity portion 110 in the product width direction W increases towards the end at the side of the rear waistline portion 30 in the product longitudinal direction L. More specifically, the low rigidity portion 110 has a wedge shape in the plan view of the disposable diaper 10. Furthermore, the boundary between the absorbent core 40*a* and the low rigidity portion 110 is formed in the shape of an arc such as a convex shape towards the center in the product width direction W.

Also, the absorber 40 has a non-stretching portion 45 that is unstretchable in the product width direction W. The non-stretching portion 45 is provided at the side of the crotch portion 25 from the sheet-like elastic element 100. Specifically, the non-stretching portion 45 is unstretchable in the product width direction W. Almost the entire absorber 40 may be unstretchable in the product width direction W. That is, as described above, the structure of the absorber 40 may be the same as in the past.

The stretch control portion 120 is formed at each of the outer sides in the product width direction W of the low rigidity portion 110. In the present embodiment, each of the stretch control portions 120 has a trapezoidal shape so as to form a convex towards the end at the side of the rear waistline portion 30. The stretch rate of the stretch control portion 120 is lower than the stretch rate of the other portions of the sheet-like elastic element 100. In the present embodiment, the stretch rate of the stretch control portion 120 is 1.0 to 1.4 times in the product width direction W. Furthermore, the contraction rate of the sheet-like elastic element 100 is 1.5 to 2.0 times in the product width direction W. The stretch rate implies the extent of stretching of the sheet-like elastic element 100 in the product width direction W, and is stipulated as below:

Stretch rate=(Length of the product during maximum extension of the sheet-like elastic element 100)/ (Length of the product in the natural state of the sheet-like elastic element 100)

The length during maximum extension is obtained by measuring the length along the product width direction W of the sheet-like elastic element 100 when the product (disposable diaper 10), in which the sheet-like elastic element 100 to be measured has been arranged, is extended to the maximum extent that the product can maintain undestroyed. Furthermore, the length in the natural state, which is the contracted state, is obtained by measuring the length along the product width direction W of the sheet-like elastic element 100 in the state when the product is kept on a flat surface and the ruggedness caused by the gathers is minimized without applying any load, as far as possible, to extend the product in the product width direction. This measurement was performed on the product after removing as much of the absorbent core 40a as possible, and also removing other elements having a stretch property.

Furthermore, the sheet-like elastic element 100 is configured such that when the sheet-like elastic element 100 is contracted in the product width direction W, the width reduction rate in the product longitudinal direction L becomes 10% or less. By setting the width reduction rate to 10% or less, the contraction of the sheet-like elastic element 100 in the product longitudinal direction L is controlled, and even when the sheet-like elastic element 100 is arranged on the hips, the shifting of the end of the rear waistline portion 30 from the predetermined position due to the contraction in the product longitudinal direction L can be controlled.

The width reduction rate is measured as described below. Firstly, take out the sheet-like elastic element 100 from the product. Keep the sheet-like elastic element 100 that has been taken out in an ambient atmosphere having a temperature of 20° C.±2° C., and a relative humidity of 60%±5% RH for 24 hours, and then set the width of the position corresponding to the center in the product width direction W during the arrangement of the sheet-like elastic element 100 in the product to the sheet-like elastic element width (WA) in the natural state.

Next, in order to check the width of the sheet-like elastic element 100 when the sheet-like elastic element 100 is extended to the width at the time of pasting on the product, in advance, measure the length along the product width direction W of the sheet-like elastic element 100 when the product is extended in the product width direction W to the maximum extent that the product can maintained undestroyed. In addition, the entire width of the sheet-like elastic element 100 that has been taken out is held between the measuring chuck of the tensile testing machine (Autograph manufactured by Shimadzu Corporation), the width of the sheet-like elastic element 100 is expanded to the extent realized at the time of pasting on the product at a speed of 100 mm/min., and then the width (WB) is measured at the position corresponding to the center in the product width direction during the arrangement of the sheet on the product in the expanded state. Use the measured WA and WB to calculate the width reduction rate with the expression described below.

Width reduction rate(%)=((WA)−(WB))/(WA)×100

In the plan view of the disposable diaper 10, the sheet-like elastic element 100 (stretching portion 105) overlaps the low rigidity portion 110 and the stretch control portion 120. In the present embodiment, the sheet-like elastic element 100 overlaps the entire low rigidity portion 110 and the stretch control portion 120, but the sheet-like elastic element 100 may overlap at least a part of the low rigidity portion 110 and the stretch control portion 120. Furthermore, the sheet-like elastic element 100 exists beyond the side edges in the product width direction W of the absorbent core 40a. That is, the width of the sheet-like elastic element 100 is wider than the width of the absorbent core 40a. The stretching portion 105 indicates the portion of the sheet-like elastic element 100 other than the portion that overlaps the low rigidity portion 110 and the stretch control portion 120.

The end at the side of the rear waistline portion 30 in the product longitudinal direction L of the sheet-like elastic element 100 is arranged between the end at the side of the rear waistline portion 30 in the product longitudinal direction L of the absorbent core 40a, and the end at the side of rear waistline portion 30 in the product longitudinal direction L of the disposable diaper 10. Furthermore, the end at the side of the crotch portion 25 in the product longitudinal direction L of the sheet-like elastic element 100 is positioned at the side of the crotch portion 25 either up to the end at the side of the crotch portion 25 of the low rigidity portion 110, or beyond the end at the side of the crotch portion 25 of the low rigidity portion 110.

The end at the side of the crotch portion 25 of the low rigidity portion 110 are positioned towards the crotch portion 25 from a tape arrangement portion A1 (see FIG. 2) provided with the pair of fastening tapes 80. On the other hand, the sheet-like elastic element 100 and a part of the low rigidity portion 110 excluding the end at the side of the crotch portion 25 exist in the tape arrangement portion A1.

The sheet-like elastic element 100 is provided so as to cover the spinous process of fifth lumbar vertebra and the left-right posterior superior iliac spine of the wearer of the disposable diaper 10. Furthermore, the low rigidity portion 110 is provided to correspond to the sacrum of the wearer.

(2) Configuration of Sheet-Like Elastic Element 100

In the present embodiment, a stretch sheet-like member is used for the sheet-like elastic element 100. The material of the sheet-like elastic element 100 is not particularly restricted, but as far as possible, a material that is thin with a low rigidity, and has a small width reduction rate is preferably used. In the present embodiment, a stretch film having a basis weight of 30 g/m² is used. The stretch film is preferably used from the viewpoint of reducing the basis weight.

When the length of the stretch film in the non-elongated state is 1.0, the stretch film is stretched up to 1.5 to 2.5 times, and is then bonded onto the backsheet 60 with a hot-melt adhesive, heat processing or the like. The stretch film is arranged between the topsheet 50 and the backsheet 60. The core wrap 40*b* may exist between the topsheet 50 and the stretch film (sheet-like elastic element 100) (see FIGS. 3(*a*) and (*b*)). Alternatively, when an exterior sheet arranged between the absorber 40 and the backsheet 60 has been provided, the stretch film may be arranged between the exterior sheet and the backsheet 60. Furthermore, when a leakage-preventing sheet is arranged intermittently in the product longitudinal direction L, the stretch film may perform the role of a leakage-preventing member. In such a case, the width of the stretch film is preferably more than the width of the absorber 40.

(3) Configuration of Absorber 40

The material of the absorber 40 is not particularly restricted, but as far as possible, a material that is thin with a low rigidity is preferably used so as to run along the body of the wearer. In the present embodiment, 170 g/m² of ground pulp and 180 g/m² of a high absorbent polymer (SAP) were used as the absorbent core 40*a*. Furthermore, 10 g/m² of an SMS nonwoven clothe was used as the core wrap 40*b*. Although the disposable diaper 10 is for infants and toddlers, the crotch width (width of the narrowest portion in the crotch portion 25) is between 50 and 100 mm, and the thinner the crotch width, the more easily the disposable diaper runs along the body of the wearer, which is preferable.

Furthermore, it is preferable to form a notch (low rigidity portion 110) to reduce the distance in the product width direction W towards the crotch portion 25, at the end of the rear waistline portion 30 of the absorbent core 40*a*. As a result of formation of such a notch, the absorber 40 does not rise even if the sheet-like elastic element 100 contracts, without inhibiting the stretching of the sheet-like elastic element 100. In view of preventing the leakage of the bodily waste, the notch is preferably narrower than the width of the sheet-like elastic element 100.

Furthermore, in the present embodiment, the stretch property of the portion, of the stretch film configuring the sheet-like elastic element 100, that corresponds to the stretch control portion 120 is removed either by heating or applying pressure in the elongated state. The stretch property may also be removed either by increasing the rigidity in the above portion than in the other portions, or by cutting the above portion very finely.

In the present embodiment, the stretch film was heated using a heating roller of 110° C. provided with a convex portion having the same pattern as the outer shape of the absorbent core 40*a*, so that the above portion did not exhibit a stretch property. When the stretch film performs the role of a leakage-preventing member, a configuration in which the stretch film is damaged, such as cutting the stretch film finely, need not be adopted.

By executing such a process, the stretch property of the low rigidity portion 110 formed between the pair of stretch control portions 120 can definitely be exhibited, and at the same time, the reduction in the surface area of the absorbent core 40*a* at the side of the clothes due to the contraction of the absorbent core 40*a* can be prevented.

(4) Operation and Effect

Figure 4A:
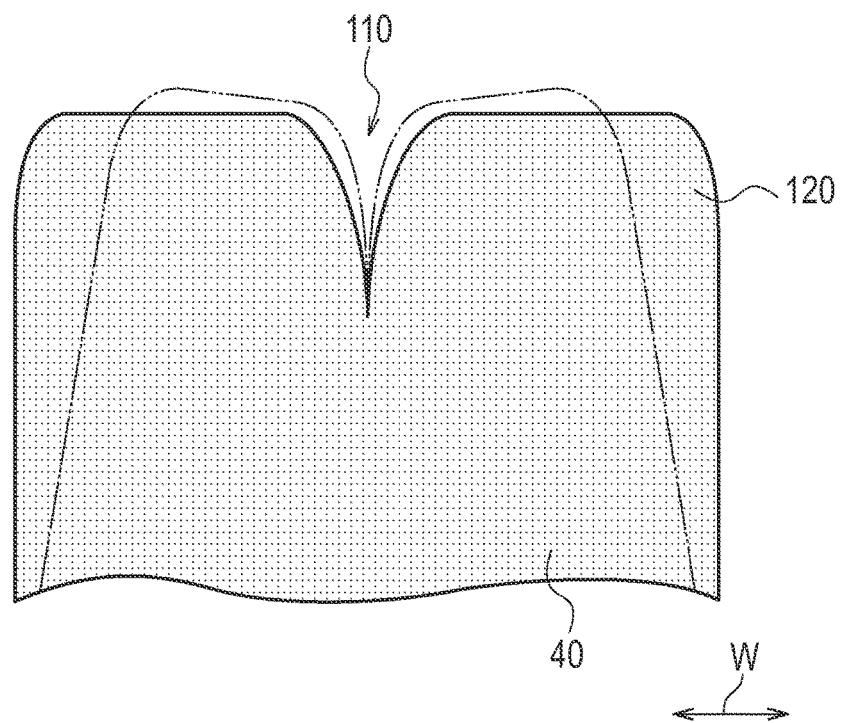
FIG. 4 is a diagram schematically illustrating the state before and after the contraction of an absorber 40 by a sheet-like elastic element 100, and the shape of the disposable diaper 10 seen from the product width direction W when the sheet-like elastic element 100 contracts according to an embodiment.
Figure 4B:
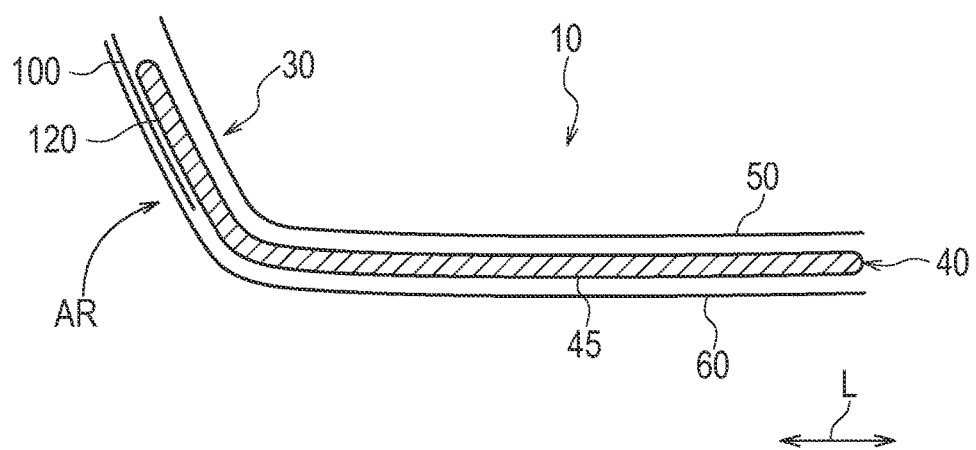

Next, the operation and effect of the disposable diaper 10 will be described. FIG. 4(*a*) schematically illustrates the state before and after the contraction of the absorber 40 by the sheet-like elastic element 100, and FIG. 4(*b*) schematically illustrates the shape of the disposable diaper 10 seen from the product width direction W when the sheet-like elastic element 100 contracts.

As illustrated in FIG. 4(*a*), when the absorber 40 contracts in the product width direction W as a result of the sheet-like elastic element 100, the low rigidity portion 110 narrows because of which the interval between the pair of stretch control portions 120 narrows. Furthermore, because the non-stretching portion 45 is formed in the absorber 40 at the side of the crotch portion 25 from the sheet-like elastic element 100, as illustrated in FIG. 4(*a*), if the interval in the product width direction W between the pair of stretch control portions 120 narrows, the rear waistline portion 30 rises in the direction of the arrow AR shown in the figure, with the area around the non-stretching portion 45 as the base point. Specifically, because the part, towards the end at the side of the rear waistline portion 30, of the low rigidity portion 110 shifts more towards the center in the product width direction W than the part towards the crotch portion 25, a difference in the amount of contraction in the product width direction W occurs between the part at the side of the rear waistline portion 30 and the part towards the crotch portion 25, because of which the rear waistline portion 30 rises.

That is, because the sheet-like elastic member 100 that can be stretched in the product width direction W, and the wedge-shaped low rigidity portion 110 are present, the disposable diaper 10 easily swells at the non-skin surface side resulting in a cup shape, when the disposable diaper 10 is worn. Additionally, because the non-stretching portion 45 is present at the side of the crotch portion 25 from the sheet-like elastic element 100, a curved portion extending in the product width direction W of the disposable diaper 10 is formed in the boundary portion between the contracted portion and the un-contracted portion, and when the non-stretching portion 45 is taken as the reference surface, the rear waistline portion 30 deforms into a state where it rises further up than the reference surface. Therefore, the disposable diaper 10 itself deforms so as to run along the curve in the back and the hips of the wearer, which makes it difficult to generate a gap between the disposable diaper and the body of the wearer, also making it difficult to generate a shift or a gap around the lower back at the dorsal side. In other words, according to the disposable diaper 10, because an element that forms a cup shape in the product width direction W, and an element that forms a cup shape in the product longitudinal direction L are both provided, it is easy to run along the body of the wearer who often adopts a C-shaped curved posture.

Furthermore, in the present embodiment, because the absorbent core 40*a* does not exist in the low rigidity portion 110, and the sheet-like elastic element 100 exists so as to overlap the low rigidity portion 110, the part towards the end at the side of the rear waistline portion 30 in the product longitudinal direction L shifts more towards the center in the product width direction W than the position of the end of the absorbent core 40*a* because of which the rise of the rear waistline portion 30 becomes more remarkable, and the above-mentioned cup shape can be formed in a more stable manner.

In the present embodiment, because the sheet-like elastic element 100 exists beyond the side edges in the product width direction W of the absorbent core 40a, the disposable diaper 10 can be formed in the shape of a cup, and at the same time, the absorbent core 40a positioned towards the end at the side of the rear waistline portion 30 in the product longitudinal direction L can actively run along the body of the wearer. Furthermore, because at least a part of the sheet-like elastic element 100 and the low rigidity portion 110 exists in the tape arrangement portion A1, even when the disposable diaper 10 is worn by spreading the disposable diaper 10 and then making the wearer lie down on the disposable diaper, the sheet-like elastic element 100 that exists beyond the side edges in the product width direction W of the absorbent core 40a is not placed under the body of the wearer, and as a result, by pulling the fastening tapes 80, the side edges of the sheet-like elastic element 100 elongate, and the disposable diaper can be more surely made to run along the body of the wearer while maintaining the position towards the cup-shaped waist.

In the present embodiment, the sheet-like elastic element 100 has the pair of non-stretching portions 45 where the stretch in the product width direction W is more controlled than that in the other portions. Therefore, in addition to the above-mentioned fact that a cup shape in which the disposable diaper 10 swells at the non-skin surface side can be formed easily, the surface area of the absorbent core 40a is maintained, enabling the prevention of leakage of bodily waste from the ends of the absorbent core 40a.

In the present embodiment, the low rigidity portion 110 is in the shape of a wedge, and the boundary between the absorbent core 40a and the low rigidity portion 110 is formed in the shape of an arc such as a convex shape towards the crotch portion 25. The radius of the arc is between 50 mm and 200 mm. Therefore, the width in the product width direction W of the low rigidity portion 110 increases non-linearly towards the end at the side of the rear waistline portion 30 in the product longitudinal direction L, because of which the rise of the rear waistline portion 30 becomes more remarkable, and the cup shape can easily be formed in a more stable manner. Additionally, because the boundary between the absorbent core 40a and the low rigidity portion 110 is formed in the shape of an arc such as a convex shape towards the crotch portion 25, due to the contraction of the low rigidity portion 110, the rear waistline portion 30 takes the shape of a rounded cup, which can easily run along the rounded hips of the wearer.

In the present embodiment, the end at the side of the crotch portion 25 of the low rigidity portion 110 is positioned towards the crotch portion 25 from the tape arrangement portion A1. Therefore, the position that forms the apex of the cup shape does not cross the portion where the disposable diaper 10 is pressed against the body of the wearer, making it difficult for the cup shape to be deformed even when the wearer moves.

In the present embodiment, the free end 72 of the solid gathers 70 is fixed on the absorbent chassis 35 along with the fixed end 71, at the end in the product longitudinal direction L, and the solid gathers 70 are fixed at the position overlapping the absorbent core 40a at the end at the side of the rear waistline portion 30. Therefore, the distance between the left and right support points (fixed ends 71) at the side of the rear waistline portion 30 of the free end 72 is narrow at the side of the rear waistline portion 30, and widens towards the side of the crotch portion 25. As a result of such a configuration, the left and right solid gathers 70 are prevented from entering inside the space between the left and right hips, particularly, in the crotch portion 25, and because the distance between the left and right solid gathers 70 at a position corresponding to the non-stretching portion 45 can be formed in the shape of a wide cup, the space in which the bodily waste can be retained is widened thus enabling the prevention of leakage of bodily waste.

In the present embodiment, the sheet-like elastic element 100 is provided so as to cover the sacrum and the left-right posterior superior iliac spine of the wearer of the disposable diaper 10. Furthermore, the low rigidity portion 110 is provided to correspond to the sacrum of the wearer. Therefore, the cup shape formed as a result of the rise of the rear waistline portion 30 is at the most appropriate position with respect to the body of the wearer, and the gap formed between the disposable diaper and the body of the wearer can be minimized.

(5) Other Embodiments

As described above, the content of the present invention is disclosed through the embodiment. However, it should not be interpreted that the statements and drawings constituting a part of the present disclosure limit the present invention. From this disclosure, a variety of alternate embodiments, examples, and applicable techniques will become apparent to one skilled in the art.

Figure 5:
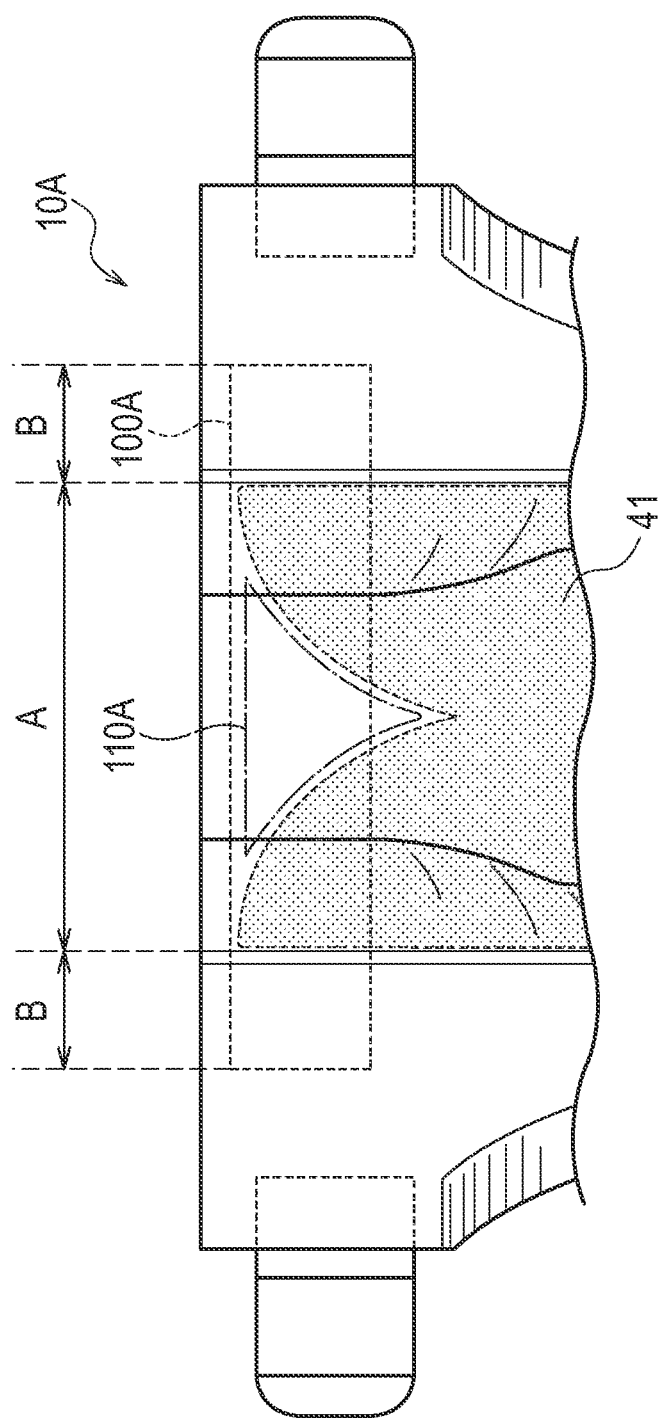
FIG. 5 is an enlarged plan view of a part of a rear waistline portion of a disposable diaper 10A according to a modification of the embodiment.

For example, the embodiment can be changed as follows: FIG. 5 is an enlarged plan view of a part of a rear waistline portion of a disposable diaper 10A according to a modification of the embodiment. As illustrated in FIG. 5, in the disposable diaper 10A, an end at the side of the rear waistline portion in the product longitudinal direction L of a sheet-like elastic element 100A is provided to overlap the end at the side of the rear waistline portion in the product longitudinal direction L of an absorber 41. Furthermore, an end at the side of a crotch portion of a low rigidity portion 110A is positioned towards the crotch portion of the disposable diaper 10A from the end at the side of the crotch portion of the sheet-like elastic element 100A.

Furthermore, the stretch rate in the A portion illustrated in FIG. 5, specifically the portion in which the absorbent core 40a exists, and the stretch rate in the B portion, specifically the portion at the outer side in the product width direction W of the absorbent core 40a, must preferably satisfy the relationship A>B. For example, if the stretch rate in the A portion is between 2.0 and 4.0 times, the stretch rate in the B portion may be between 1.5 and 2.0 times.

According to such a disposable diaper 10A, the low rigidity portion 110A can be contracted more easily, and therefore, the cup shape of the disposable diaper 10A can be formed in a stable manner. Furthermore, because the rear waistline portion 30 including the B portion can be prevented from contracting too much, when the disposable diaper 10A is spread under the wearer and then put on, the difficulty in pulling the rear waistline portion 30 and the fastening tapes 80 can be prevented.

Furthermore, in the aforementioned embodiment, the end in the product longitudinal direction L of leg gathers 75 overlapped the end in the product longitudinal direction L of the sheet-like elastic element 100 in the product longitudinal direction L, however, such a structure may not necessarily be present. In the aforementioned embodiment, because the portion of the disposable diaper running along the body of the wearer due to the cup shape is pulled in towards the crotch portion 25 of the wearer due to the leg gathers 75, when the surface of the skin of the wearer stretches and contracts due to standing and sitting, the waist end at the back may shift easily. If the ends are not to overlap, then it is possible to prevent such a situation from occurring.

In the aforementioned embodiment, the fastening tapes 80 were provided in the rear waistline portion 30, but the fastening tapes 80 need not necessarily be provided in the rear waistline portion 30, and can be provided in the front waistline portion 20.

In the aforementioned embodiment, a disposable diaper used for infants and toddlers was cited as an example, however, the present invention can be applied not only to a disposable diaper for infants and toddlers, but can also be suitable applied to a disposable diaper used for adults, particularly, elderly people who may easily adopt a C-shaped curved posture.

In the aforementioned embodiment, an open-type disposable diaper was described as an example, however, the present invention is also applicable to a pant-type disposable diaper. In a pant-type disposable diaper, the portion corresponding to the tape arrangement portion A1 is preferably the portion at the joining part of both sides.

As described above, it is of course that the present invention includes various embodiments and the like not described here. Therefore, the technical range of the present invention is to be defined only by the inventive specific matter according to the adequate claims from the above description.

In addition, the entire content of Japanese Patent Application No. 2011-289647 (filed on Dec. 28, 2011) is incorporated in the present specification by reference.

INDUSTRIAL APPLICABILITY

According to the characteristics of the present invention, it is possible to provide a disposable diaper having an improved fitting for wearers who may easily adopt a C-shaped curved posture, such as infants.

The invention claimed is:

1. A disposable diaper, comprising:
a front waistline portion,
a rear waistline portion,
a crotch portion positioned between the front waistline portion and the rear waistline portion,
an absorber spanning the crotch portion and extending in the front waistline portion and the rear waistline portion,
a product longitudinal direction from the front waistline portion towards the rear waistline portion, and a product width direction perpendicular to the product longitudinal direction,
a sheet-shaped elastic element provided in the rear waistline portion,
wherein
the sheet-shaped elastic element is a stretchable sheet including a stretching portion stretchable in the product width direction,
the absorber comprises:
an absorber core,
a low rigidity portion, wherein a basis weight of the low rigidity portion is lower than a basis weight of a remaining part of the absorber, or the low rigidity portion is a portion where the absorber core does not exist,
side portions located outside and on opposite sides of the low rigidity portion in the product width direction,
a non-stretching portion that is unstretchable in the product width direction, and
a pair of stretch control portions, wherein a stretch of the stretch control portions in the product width direction is more controlled than that of the other portions,
the non-stretching portion is provided, in the product longitudinal direction, between the crotch portion and the stretching portion,
the stretching portion overlaps at least a part of the low rigidity portion in a plan view of the disposable diaper when the diaper is flatly developed,
the low rigidity portion is arranged between the pair of stretch control portions in the product width direction,
the low rigidity portion extends in the product longitudinal direction up to a rear end of the absorbent core in the rear waistline portion,
a width of the low rigidity portion in the product width direction increases, in the product longitudinal direction, towards the rear end of the absorbent core in the rear waistline portion, and
the sheet-shaped elastic element straddles the low rigidity portion and the side portions.

2. The disposable diaper according to claim 1, wherein the absorbent core include side edges opposing each other in the product width direction, and
the sheet-shaped elastic element extends in the product width direction beyond the side edges of the absorbent core.

3. The disposable diaper according to claim 1, further comprising a pair of fastening tapes arranged at one of the front waistline portion and the rear waistline portion,
wherein
the absorber is arranged between the pair of fastening tapes in the product width direction,
the fastening tapes are configured to affix to the other one of the front waistline portion and the rear waistline portion,
a front end of the low rigidity portion extends towards the crotch portion from a tape arrangement portion provided with the fastening tapes, and
a part of at least one of the stretching portion and the low rigidity portion exists within the tape arrangement portion.

4. The disposable diaper according to claim 3, further comprising front and rear longitudinal ends located at the front and rear waistline portions, respectively, wherein
a rear end of the sheet-shaped elastic element in the product longitudinal direction is arranged in the product longitudinal direction between a rear end of the absorbent core and the rear longitudinal end of the disposable diaper, and
a front end of the sheet-shaped elastic element in the product longitudinal direction
overlaps the front end of the low rigidity portion, or
is positioned in the product longitudinal direction between the front end of the low rigidity portion and the front longitudinal end.

5. The disposable diaper according to claim 1, wherein when the disposable diaper is in a state as being worn on a wearer, the sheet-shaped elastic element is adapted to cover the spinous process of fifth lumbar vertebra and the left-right posterior superior iliac spine of the wearer of the disposable diaper, and the low rigidity portion is adapted to be positioned corresponding to the sacrum of the wearer.

6. The disposable diaper according to claim 1, wherein the low rigidity portion has a wedge shape in the plan view of the disposable diaper, and a boundary between the absorbent core and the low rigidity portion has an arc shape convex towards a center of the absorbent core in the product width direction.

7. The disposable diaper according to claim 1, further comprising:

an absorbent chassis including the absorber, a topsheet on a top of the absorber, and a pair of longitudinal elastic elements each having a fixed end extending along the product longitudinal direction in one of side edges of the absorber in the product width direction and fixed on the absorbent chassis, a free end configured to rise from the absorbent chassis, and longitudinal ends opposing each other in the product longitudinal direction, wherein the free end is fixed on the topsheet along with the fixed end, at the longitudinal ends of said longitudinal elastic element, and the fixed end overlaps the absorbent core at the longitudinal end of the corresponding longitudinal elastic element at the rear waistline portion.

8. The disposable diaper according to claim 1, wherein when the sheet-shaped elastic element is contracted in the product width direction, a width reduction rate of the sheet-shaped elastic element in the product longitudinal direction is 10% or less.

9. The disposable diaper according to claim 1, wherein the sheet-shaped elastic member overlaps a part of the absorbent core and the part of the low rigidity portion in the plan view of the disposable diaper when the disposable diaper is flatly developed.

10. A disposable diaper, comprising:

a front waistline portion, a rear waistline portion, a crotch portion positioned between the front waistline portion and the rear waistline portion, an absorber spanning the crotch portion and extending in the front waistline portion and the rear waistline portion, a product longitudinal direction from the front waistline portion towards the rear waistline portion, and a product width direction perpendicular to the product longitudinal direction, a sheet-shaped elastic element provided in the rear waistline portion, wherein the sheet-shaped elastic element is a stretchable sheet including a stretching portion stretchable in the product width direction, the absorber comprises:

an absorber core including side edges opposing each other in the product width direction, a low rigidity portion, wherein a basis weight of the low rigidity portion is lower than a basis weight of a remaining part of the absorber, or the low rigidity portion is a portion where the absorber core does not exist, side portions located outside and on opposite sides of the low rigidity portion in the product width direction, a non-stretching portion that is unstretchable in the product width direction, and a pair of stretch control portions, the non-stretching portion is provided, in the product longitudinal direction, between the crotch portion and the stretching portion, the stretching portion overlaps at least a part of the low rigidity portion in a plan view of the disposable diaper when the diaper is flatly developed, the low rigidity portion is arranged between the pair of stretch control portions in the product width direction, the low rigidity portion extends in the product longitudinal direction up to a rear end of the absorbent core in the rear waistline portion, a width of the low rigidity portion in the product width direction increases, in the product longitudinal direction, towards the rear end of the absorbent core in the rear waistline portion and in the plan view of the disposable diaper when the diaper is flatly developed, the sheet-shaped elastic element continuously extends in the product width direction to overlap the low rigidity portion, the side portions, and the side edges of the absorbent core.

* * * * *